United States Patent
Iversen et al.

[11] Patent Number: 5,964,803
[45] Date of Patent: Oct. 12, 1999

[54] ENHANCED SURFACE IMPLANT AND METHOD OF MANUFACTURE

[75] Inventors: Alfred Abner Iversen, Wayzata; Stephen M. Trinter, Eden Prairie, both of Minn.

[73] Assignee: PMT Corporation, Chanhassen, Minn.

[21] Appl. No.: 08/840,969

[22] Filed: Apr. 21, 1997

Related U.S. Application Data

[60] Continuation-in-part of application No. 08/490,283, Jun. 14, 1995, abandoned, which is a division of application No. 08/097,564, Jul. 27, 1993, Pat. No. 5,525,275.

[51] Int. Cl.$^6$ ........................................... A61F 2/12
[52] U.S. Cl. ............................................................ 623/8
[58] Field of Search ................................. 623/8, 11, 66, 623/12, 901

[56] References Cited

U.S. PATENT DOCUMENTS

| | | |
|---|---|---|
| 3,293,663 | 12/1966 | Cronin . |
| 3,366,975 | 2/1968 | Pangman . |
| 3,559,214 | 2/1971 | Pangman . |
| 3,852,832 | 12/1974 | McGhan et al. . |
| 3,936,517 | 2/1976 | Thomas . |
| 4,143,109 | 3/1979 | Stockum . |
| 4,178,643 | 12/1979 | Cox, Jr. . |
| 4,190,040 | 2/1980 | Schulte . |
| 4,217,889 | 8/1980 | Radovan et al. . |
| 4,298,997 | 11/1981 | Rybka . |
| 4,455,691 | 6/1984 | Redinger et al. . |
| 4,472,226 | 9/1984 | Redinger et al. . |
| 4,481,335 | 11/1984 | Stark, Jr. . |
| 4,531,244 | 7/1985 | Hamas . |
| 4,543,088 | 9/1985 | Bootman et al. . |
| 4,643,733 | 2/1987 | Becker . |
| 4,648,880 | 3/1987 | Brauman . |
| 4,662,883 | 5/1987 | Bell et al. . |
| 4,666,447 | 5/1987 | Smith et al. . |
| 4,671,255 | 6/1987 | Dubrul et al. . |
| 4,735,982 | 4/1988 | Orndorff, Jr. . |
| 4,738,657 | 4/1988 | Hancock et al. . |

(List continued on next page.)

OTHER PUBLICATIONS

S. R. Taylor and D. F. Gibbons, "Effect of Surface Texture on the Soft Tissue Response to Polymer Implants", Journal of Biomedical Materials Research, vol. 17, 1983, pp. 205–227.

Professor K. Gerhard Brand's letter to Dr. R. K. Donis.

George J. Picha and Dennis J. Siedlak, "Ion–Beam Microtexturing of Biomaterials", MDGDI, Apr., 1984, pp. 39–42.

"Proven Generation", The Becker Expander/Mammary Prosthesis, Nov., 1987.

Steven Herman, M.D., "The Meme Implant", Plastic and Reconstructive Surgery, Mar., 1984, pp. 411–414.

Thomas D. Rees, M.D., et al., "The Use of Inflatable Breast Implants", Plastic and Reconstructive Surgery, Dec., 1973, pp. 609–615.

Surgitek Gel/Saline Mammary Implant, Jan., 1984.

(List continued on next page.)

*Primary Examiner*—Bruce E. Snow
*Attorney, Agent, or Firm*—Anthony G. Eggink

[57] ABSTRACT

An implantable body including an outer membrane forming an enclosure for receiving a filler material. The surface of the outer membrane is characterized by a random distribution of peaks separated by valleys. The peaks and valleys are separated by gradual contoured slopes with a smooth transition between the peaks and valleys which are substantially free from indentation. The enhanced surface provides improved anchoring of the implant, yet reduces host reaction. The enhanced surface is formed by depositing a distribution of cured polymeric particles on an uncured tacky surface. This intermediate surface is then cured, followed by application of a layer of uncured elastomeric material. The entire surface is then cured to form the enhanced surface.

32 Claims, 4 Drawing Sheets

U.S. PATENT DOCUMENTS

| | | |
|---|---|---|
| 4,772,284 | 9/1988 | Jefferies et al. . |
| 4,775,379 | 10/1988 | Fogarty et al. . |
| 4,798,584 | 1/1989 | Hancock et al. . |
| 4,840,615 | 6/1989 | Hancock et al. . |
| 4,841,948 | 6/1989 | Bauer et al. . |
| 4,859,712 | 8/1989 | Cox . |
| 4,889,744 | 12/1989 | Quaid . |
| 4,890,866 | 1/1990 | Arp . |
| 4,930,535 | 6/1990 | Rinehold . |
| 4,944,749 | 7/1990 | Becker . |
| 4,955,909 | 9/1990 | Ersek et al. . |
| 4,960,425 | 10/1990 | Yan et al. . |
| 4,992,312 | 2/1991 | Frisch . |
| 5,002,572 | 3/1991 | Picha . |
| 5,005,591 | 4/1991 | Austad . |
| 5,007,929 | 4/1991 | Quaid . |
| 5,019,101 | 5/1991 | Purkait et al. . |
| 5,022,942 | 6/1991 | Yan et al. . |
| 5,083,576 | 1/1992 | Ruiz-Razura et al. . |
| 5,092,348 | 3/1992 | Dubrul et al. . |
| 5,116,370 | 5/1992 | Foglietti . |
| 5,138,719 | 8/1992 | Orlianges et al. . |
| 5,196,263 | 3/1993 | Melby et al. . |
| 5,201,715 | 4/1993 | Masters . |
| 5,236,453 | 8/1993 | Picha . |
| 5,236,454 | 8/1993 | Miller . |
| 5,354,338 | 10/1994 | Ledergerber . |
| 5,480,430 | 1/1996 | Carlisle et al. . |
| 5,496,370 | 3/1996 | Hamas . |

OTHER PUBLICATIONS

Hilton Becker, M.D., "Breast Reconstruction Using an Inflatable Breast Implant with Detachable Reservoir", Plastic and Reconstructive Surgery, Apr., 1984, pp. 678–683.

James C. Sipio, M.D., et al., "Soft Tissue Expansion of the Ureter and Bladder in the Dog", Sep., 1986.

Francis A. Marzoni, M.D., et al, "An Experimental Study of Silicone as a Soft Tissue Substitute", Plastic and Reconstructive Surgery, Dec., 1959.

Julio C. Davila, et al, Some Physical Factors Affecting the Acceptance of Synthetic Materials as Tissue Implants, 1968.

Benjamin F. Edwards, M.D., "Teflon–Silicone Breast Implants", Plastic and Reconstructive Surgery, Nov., 1963, pp. 519–526.

Robert L. Whalen, "Improved Textured Surfaces for Implantable Prosthesis", Trans Am Soc Artif Intern Organs, 1988, vol. XXXIV, pp. 887–892.

McGhan Biocell Textured Mammary Implant, Oct., 1987.

V.R. Pennisi, M.D., "Polyurethane–Covered Silicone Gel Mammary Prosthesis for Successful Breast Reconstruction", Aesthetic Plastic Surgery, 1985.

Franklin L. Ashley, M.D., "A New Type of Breast Prosthesis", Plastic and Reconstructive Surgery, May, 1970, pp. 421–424.

D. W. Brown, et al, "The Kinetics of Hydrolytic Aging of Polyester Urethane Elastomers", Jul., 1979.

Roger T. Sherman, M.D., et al, "The Biological Fate of Implanted Rigid Polyurethane Foam", Journal of Surgical Research, Mar., 1969, pp. 167–171.

ENHANCED SURFACE IMPLANT AND METHOD OF MANUFACTURE

This is a continuation-in-part of U.S. Ser. No. 08/490,283 filed Jun. 14, 1995 now abandoned, which is a division of U.S. Ser. No. 08/097,564 filed Jul. 27, 1993, U.S. Pat. No. 5,525,275.

TECHNICAL FIELD

The present invention relates to implantable bodies for humans. More specifically, the invention is directed to an implantable body having an improved outer membrane surface and a method of manufacturing an implantable body with such an enhanced surface. The enhanced surface is economical to create and facilitates proper anchoring to the tissue surrounding the body upon implantation, yet reduces the host's natural encapsulation reaction to the implant.

BACKGROUND OF THE INVENTION

Implantable devices, particularly mass transfer devices, breast implants, prosthesis and tissue expanders, are generally known. Many of these devices include a sack-like or envelope-like bladder which is manufactured from an elastomeric material such as silicone rubber and then filled with a liquid or gel. The liquid or gel filling can be a silicone fluid or a saline solution. A combination of an elastomeric envelope and liquid or gel fill material is utilized to imitate properties of the tissue being replaced or supplemented in breast implants. An expander may be an expandable bladder with a local or remote port to add or remove liquid or gel. In tissue expanders, the same general design allows variable degrees of expansion.

Initially developed soft pliable prosthetic implants included a smooth surface. It was felt that the smooth surface would elicit a minimal foreign body reaction. This was found to be true, however, the smooth surface prevented attachment of the scar capsule to the prosthesis so that any movement of the host created a shearing effect which lead to a later and perhaps more severe encapsulation response if the prosthesis was subject to trauma or some sort of infection in the area of implant.

Picha, in U.S. Pat. No. 5,002,572, discloses that it is known that the implantation of an article or material into soft tissue initiates a sequence of physiological events in which the body attempts to remove or isolate the foreign entity. The presence of an implant may lead to the formation of a collagen layer of increased density as part of the host's attempt to isolate the foreign body. Such layers are referred to as the "fibrous capsule" and its formation is dependent upon a multiplicity of factors including surgical procedure, implant shape and size, relative movement between and surrounding tissue, and surface morphology of the implant or texture.

Picha discloses an implant in which the surface of the device in tissue contact is molded to provide a regular pattern of micropillars at least 100 microns ($\mu$m) in height with transverse dimensions and interpillar spacing each no greater than 5000 microns. Picha discloses that micropillars have been found to influence the density, vascularity, and cellularity of the capsule surrounding the implant.

Ersek et al., in U.S. Pat. No. 4,955,909, disclose that capsular contracture causing firmness of soft silicone implants is a serious problem that may result from several causative factors that have, as their final pathway, the development of increased scar tissue. Ersek et al. state that this problem may be reduced by forming a net-like three-dimensional grid on the silicone surface in order to gain fibroblast ingrowth into the interstices and thus prevent micromotion at the host prosthesis interface.

G. Picha and D. Siedlak, in "Ion-Beam Microtexturing of Biomaterials", *MD and DI*, pp. 39–42 (April, 1984), disclose a method to manufacture uniform pillar projections on the surface of an implant using ion-beam thruster technology. Although this method overcomes the disadvantages of the open cell method (discussed below), it is believed a costly process and uneconomical to apply to custom-shaped surfaces.

Figure 4:
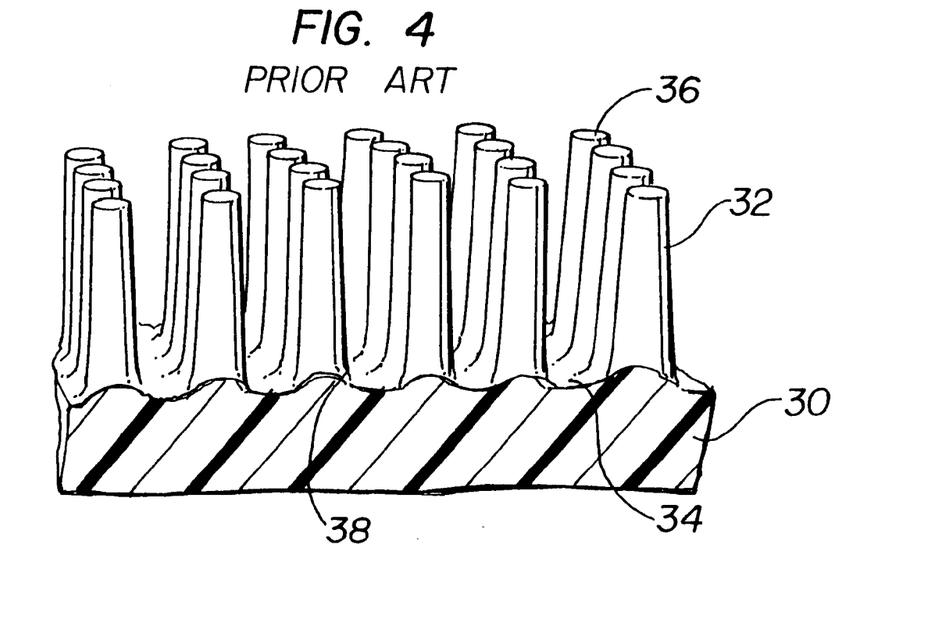
FIG. 4 is a greatly enlarged cross-sectional view of the regular textured surface of a prior art implant surface.

The pillar surface structure of Picha '572, Ersek et al. '909 and Picha and Siedlak ion-beamed surfacing technology is generally depicted in FIG. 4.

Figure 5:
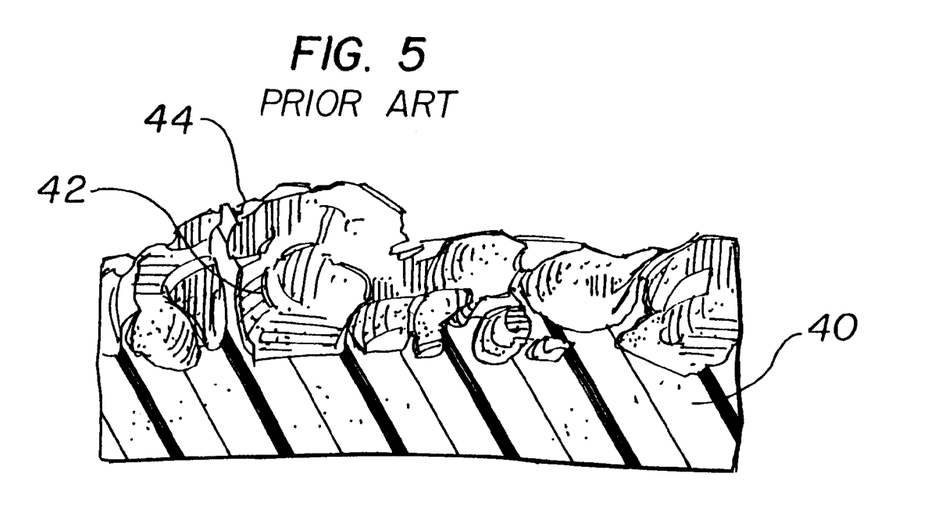
FIG. 5 is a greatly enlarged cross-sectional view of a prior art open-celled, textured surface.

In U.S. Pat. No. 4,889,744, issued to Quaid, a method for making a medical implant with an open cell textured surface is disclosed. The implant has an open cell texture produced by applying soluble particles (e.g., salt, sugar, etc.) to an uncured layer of silicone dispersion. The silicone layer is then fully cured. Subsequent to curing, the silicone layer is then placed in a suitable solvent so that the solid particles are dissolved from the surface of the shell. This method creates open cells on the surface of the implantable body. This prior art device is depicted in FIG. 5.

The open cell structure manufacturing technique is believed to pose three potential problems. First, introduction of a foreign or non-silicone particle to the surface of the uncured silicone can affect the properties of the silicone during the curing process or over the life of the implant. The open cell structure also creates potential silicone fragments which can easily become detached from the open cell structure or cell wall as can be readily seen by the physical shape of the cells in FIG. 5. Finally, use of a soluble particle requires that the particle be fully dissolved prior to implant. If the particle is not fully dissolved or the particle becomes encapsulated by the silicone, such particles may be released from the surface after implantation. This may be detrimental.

Thus, it is generally known to alter the surface morphology or topology of an implantable device to improve the host prosthesis interface. It will also be appreciated that the selection of an altered surface configuration requires balancing between having sufficient texturing to provide adequate anchoring of the implant and having a textured design which minimizes adverse body reaction. Thus, the ideal implant provides sufficient anchoring while minimizing the encapsulation response and subsequent scar tissue.

Other considerations in selecting the technology for altering or texturing the implantable device include the cost of the method, along with any potential hazards the method may create in the final implantable device. As was seen with the open cell textured method, the potential for contamination from the soluble particles or fragmentation of a cell wall may pose a problem. Further, the ion-beam thruster method may be considered uneconomical.

Accordingly, a need exists for an improved or enhanced implant surface morphology or topology which provides sufficient anchoring at the host prosthesis interface while minimizing the reaction of the human body to the foreign body implant. Further, a method to manufacture such enhanced surface is needed. The selected implant enhanced surface should also have a closed cell structure without interstices which is economically manufactured. The present invention addresses these needs as well as other problems associated with existing textured surface implants. The present invention also offers further advantages over the prior art and solves other problems associated therewith.

SUMMARY OF THE INVENTION

The present invention is an improved, enhanced, random sculptured, undulating surface implant which is soft and pliable for implantation in humans. The implant has an outer membrane forming an enclosure suitably for a filler material and an outer surface treated for host-implant interface. The implant of the present invention is particularly useful as a breast implant, prosthesis, mass transfer device or a tissue expander.

The implant or prosthesis of the present invention includes an undulating sculptured surface disposed over at least a portion of the outer membrane surface. The undulating enhanced surface is characterized by a random or irregular distribution of peaks separated by valleys. The peaks and valleys have gradual contoured slopes and terraces therebetween.

The undulating enhanced surface is further characterized by generally smooth transitions between peaks and valleys. The transitions are substantially free of indentations and interstices which may trap body fluids. The undulating surface provides improved anchoring of the implant, yet reduces host reaction.

The enhanced surface implantable body can include an outer membrane forming an enclosure for receiving a filler material. The filler material may be included in the implant when purchased. The filler material may be a fluid or gel.

In a preferred embodiment, the mean peak to surface height differential may illustratively be 800 $\mu$m to 2500 $\mu$m (0.031" to 0.10"). The spacing between peaks may be about 600 $\mu$m (0.024"). Further, the entire outer membrane surface can have disposed thereon the undulating enhanced surface. The smooth transitions between peaks and valleys can further include terraced contours and slopes. The undulating textured surfaces are preferably free of open cells.

The sculptured enhanced surface of the present implant is formed by first providing an elastomeric material suitable for use as an implant which has a tacky surface. This material may be an uncured silicone rubber. The silicone rubber may be dispersed in a solvent and applied to a mandrel.

Cured polymeric particles are randomly deposited on the tacky surface to form an intermediate textured surface. The cured polymeric particles may be silicone particles which are ground to a specific size, preferably under cryogenic conditions. The polymeric particles in a preferred method have an average diameter of 300 $\mu$m to 600 $\mu$m (0.012" to 0.024"). It is recognized however, that the size and distribution of particles may be varied with resulting variations in the degree of surface enhancement. Further, the quantity of polymeric particles which are deposited on the tacky surface will also affect the surface enhancement. Also, it is known that the particles stack on one another due to frictional and static forces, resulting in peaks higher than the average particle size.

Preferably, the polymeric particles are tetrahedral in shape. Such a shape results when silicone is cryogenically ground due to physical and surface tension forces because a tetrahedron is the most efficient body in the universe.

The tacky surface having the deposited random distribution of cured polymeric particles, the intermediate enhanced surface, is then cured. Curing of this surface includes heating the material to a temperature between 130° F. and 270° F. for approximately one hour.

A layer of uncured elastomeric material, suitably on a mandrel, is then applied over the intermediate textured surface after it has been cured. The uncured elastomeric material is preferably a silicone rubber dispersed in a solvent into which the mandrel is dipped.

Upon applying the layer of uncured elastomeric material, the intermediate enhanced surface having the layer applied thereon is cured to form the undulating sculptured, irregular enhanced surface. Curing of the intermediate enhanced surface having the applied layer of uncured elastomeric material includes heating to a temperature between 130° F. and 270° F. for approximately one hour.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE INVENTION

As required, detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the present invention.

Figure 1:
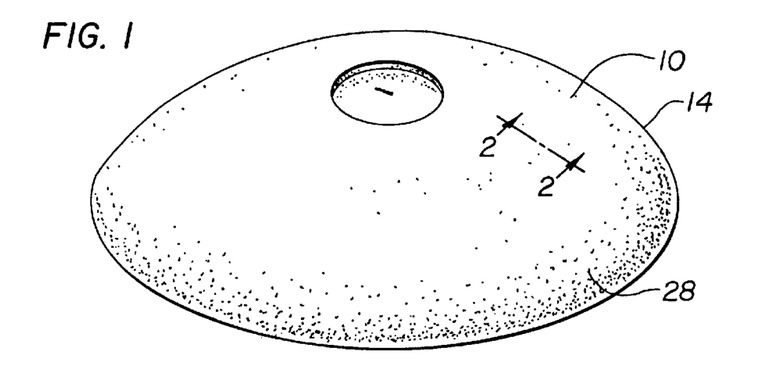
FIG. 1 is a perspective view of an implant having an undulating enhanced surface of the present invention.

FIG. 1 is a perspective view of a textured implantable body or prosthesis 10 which may or may not be expandable. The textured implantable body 10 includes an outer membrane which forms an enclosure for receiving a filler material. A filler material may be added to the membrane prior to or during surgery.

Figure 2:
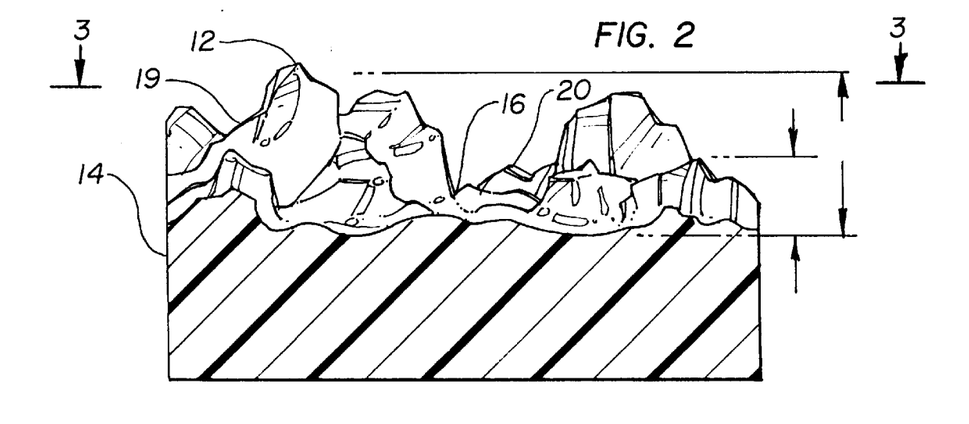
FIG. 2 is a greatly enlarged cross-sectional view taken along a line 2—2 of FIG. 1, illustrating the enhanced surface.

FIG. 2 is a greatly enlarged cross-sectional view of the outer membrane along line 2—2 of FIG. 1. As depicted in FIG. 2, the cross-section includes a thickness of elastomeric material 14 exhibiting an enhanced surface 19. The surface 19 is an undulating sculptured surface which is disposed over at least a portion of the outer membrane surface. The undulating textured surface 19 is characterized by a random or irregular distribution of peaks 12 separated by valleys 16. The peaks 12 and valleys 16 are separated by gradual contoured slopes 20.

The undulating textured surface 19 is further characterized by generally smooth transitions between the peaks 12 and valleys 16. The transitions are substantially free of indentations, interstices or open cells, which may trap body fluids or cause irritation at the host prosthesis interface. Thus, the undulating surface 19 provides improved anchoring of the prosthesis 10 yet reduces host reaction.

Figure 3:
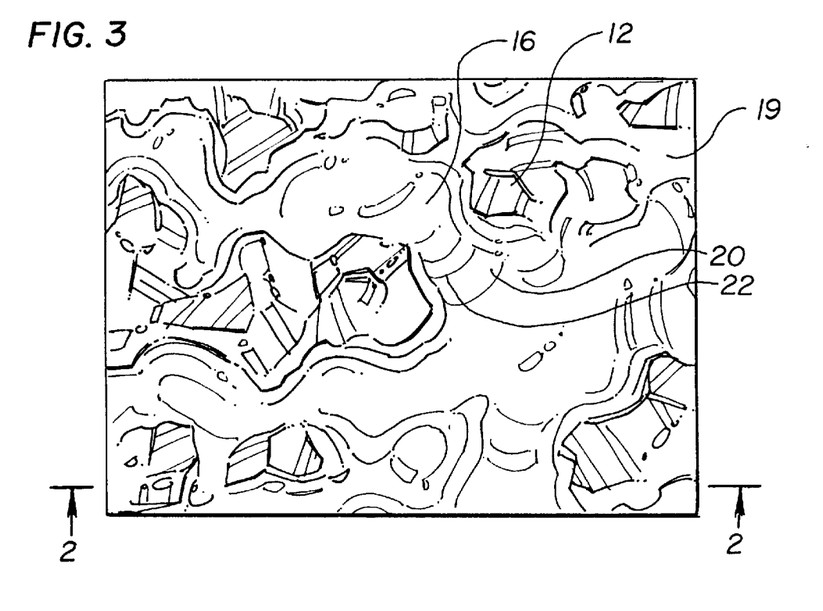
FIG. 3 is a greatly enlarged fragmentary top plan view taken along lines 3—3 of FIG. 2 showing the general shape of the contoured enhanced surface.

FIG. 3 illustrates a greatly enlarged fragmentary view of the enhanced surface 19 in plan view. The slopes 20 leading from peaks 12 to valleys 16 are depicted as contours 22 which are terraced along the transition between peaks 12 and valleys 16. This transition is generally smooth. Because the undulating enhanced surface 19 of the present invention is difficult to describe, FIGS. 4 and 5 have been included for comparison of the surface 19 topology or morphology of the present implant 10 with the surface achieved with prior art surface texturing methods as described above in the background.

FIG. 4 depicts a surface texture which includes a fixed array of pillars 32. As depicted, the membrane outer surface includes a layer of elastomeric material 30 on which pillars 32 are formed. The pillars 32 as characterized by sharp transitions 38 from valleys 34 and rise to plateaued peaks 36. As is clearly visible, the texture is designed to provide strong anchoring of the implant at the host prosthesis interface.

FIG. 5 depicts another prior art textured surface which is manufactured by placing soluble crystals on the uncured elastomeric material. Subsequent to curing, the soluble particles are dissolved to leave a texture surface. The prior art textured surface includes a layer of elastomeric material 40 on which the textured surface lies. The textured surface is characterized by void volumes or pits 42 which are formed by dissolving the crystals on the surface, such as sugar or salt. Thus, the surface is covered with pits and cavities which provide the means for anchoring the prosthesis at the host prosthesis interface. The peaks 44 generally include sharp or fragmentary edges with sharp transitions to valleys with open cells substantially covering the surface.

Figure 6:
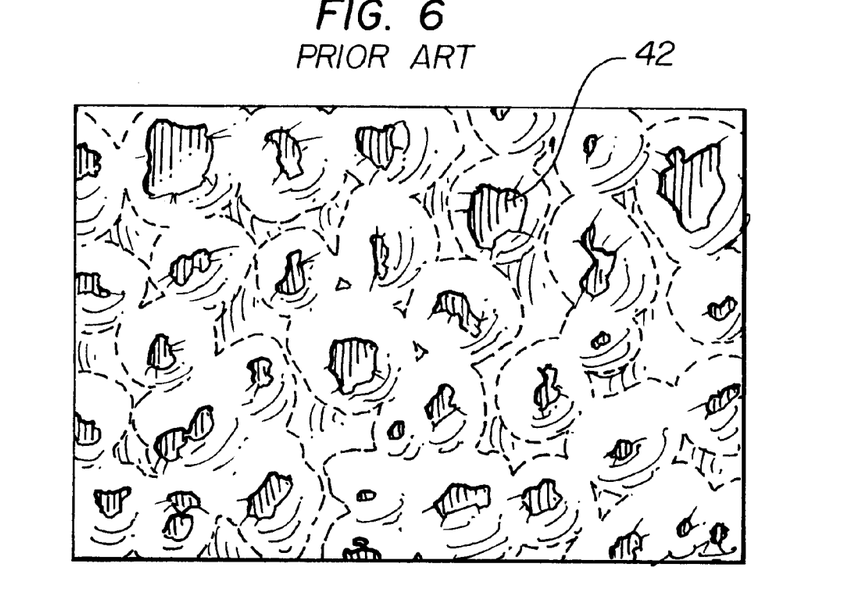
FIG. 6 is a greatly enlarged fragmentary top plan view of a prior art prosthesis of open cells.

FIG. 6 depicts the textured surface of a prosthesis according to U.S. Pat. No. 5,092,348, which was obtained by photomicrography. The surface shows many void volumes or pits 42.

Figure 7:
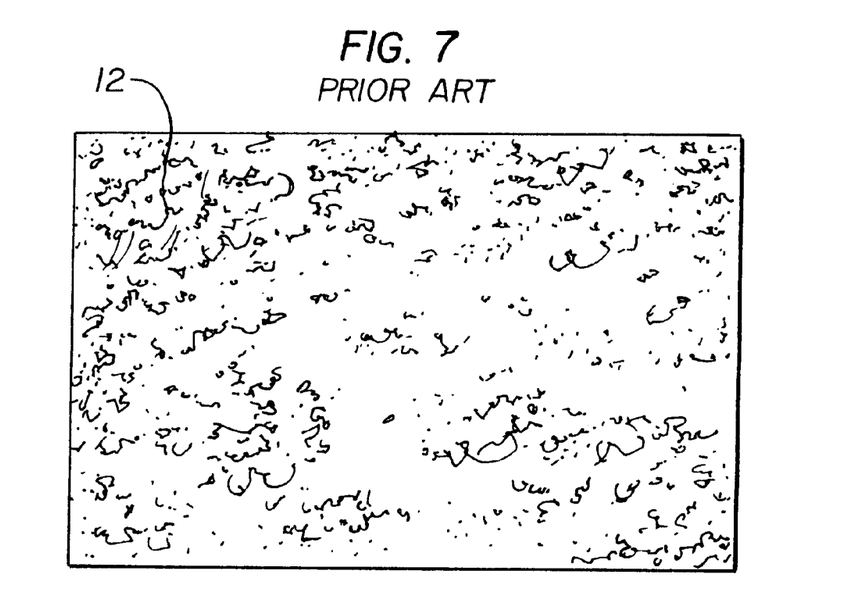
FIG. 7 is a greatly enlarged fragmentary top plan view of another prior art prosthesis.

FIG. 7 depicts the textured surface of a prosthesis according to U.S. Pat. No. 4,960,425, obtained by photomicrography. As can be seen, the textured surface consists of peaks 12 which according to the specification of the '425 patent are 0.0003" to 0.030" high (Col. 5, lines 6–8). This produces an opaque surface, slightly rough to the touch (Col. 5, lines 8–10), which is totally different from the textured surface 19 of the present invention which has peaks 12 of 800 $\mu$m to 2500 $\mu$m (0.031" to 0.100") high and much more widely spaced. Furthermore, FIG. 10 of the '425 patent shows indentations which range in depth from 0.0003" to 0.030" (Col. 5, lines 6–8). The surface 19 of the present invention is substantially free of such indentations.

The preferred prosthesis 10 of the present invention includes mean peak 12 to surface 16 differentials ranging from 800 $\mu$m to 2500 $\mu$m (0.031" to 0.100"). Preferably, the entire outer surface has disposed thereon an undulating textured surface 19. The surface 19 is also substantially free of open cells.

The undulating surface 19 of the present invention may be formed by at least one process which assists in defining and understanding the enhanced surface 19. Generally, the process begins with providing an elastomeric material suitable for use in an implant which has a tacky surface 18. The preferred material is an uncured silicone rubber. The silicone is preferably dispersed in a solvent, as is commonly known, into which a forming mandrel is dipped.

Figure 8:
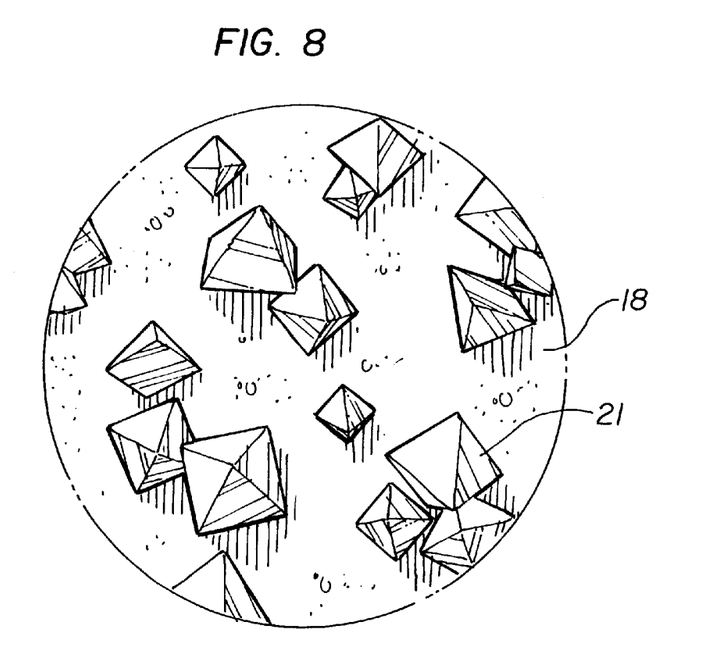
FIG. 8 is a conceptual drawing showing the polymeric particles of the present invention stacking on one another.
Figure 9:
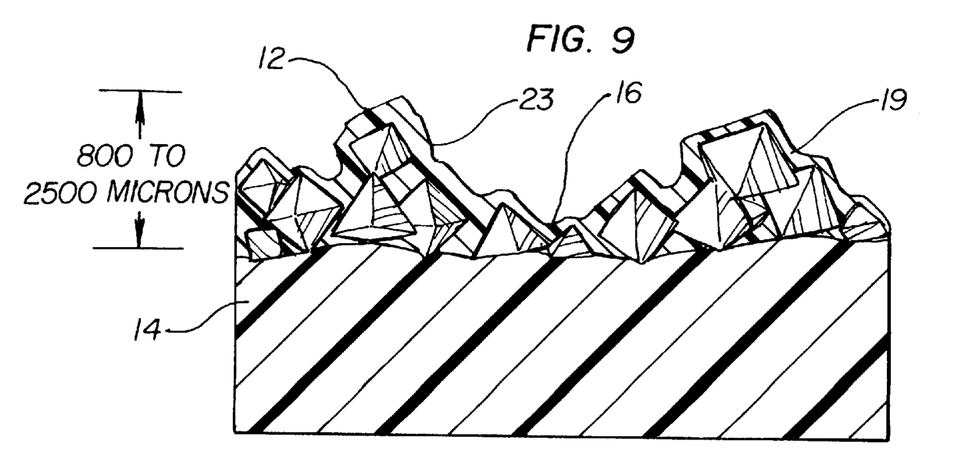
FIG. 9 is a greatly enlarged cross-sectional view taken along line 2—2 of FIG. 1 with the polymeric particles shown stacked on one another.

A distribution of cured polymeric particles 21 is then deposited on the tacky surface 18 to form an intermediate textured surface. The polymeric particles 21 are silicone particles which have been ground to a desired diameter and particle distribution. As discussed in the example below, the grinding is preferably completed cryogenically. The polymeric particles 21 can have an average diameter that is in a range of 300 $\mu$m to 600 $\mu$m (0.012" to 0.024") but generally less than 500 $\mu$m (0.02"). The particles 21 are preferably tetrahedral in shape as shown in FIG. 8 and stack on one another. This stacking produces the preferred peak 12 height of 800 $\mu$m to 2500 $\mu$m, as shown in FIG. 9.

The intermediate textured surface is then cured. The curing step includes heating to a temperature between 130° F. and 270° F. for about one hour.

A layer of uncured elastomeric material 23 is applied over the intermediate textured surface. This material is again preferably dispersed in a solvent. The preferred uncured elastomeric material is uncured silicone rubber. This material is then cured to form the undulating enhanced surface 19. The step of curing the intermediate surface having the applied layer of uncured elastomeric material includes heating to a temperature of about 130° F. to 270° F. for about one hour.

The following method is offered illustratively and is not to be viewed as limiting. Other methods of manufacture may also achieve the enhanced surface 19 of the present invention.

EXAMPLE 1

Method of Producing a Textured Surface Implant

The following procedure was utilized to produce an implant with the textured or enhanced surface of the present invention:

1. Producing the Particulate
   a. Silicone feed material was placed in a grinding unit, suitable for cryogenic grinding.
   b. Liquid nitrogen was added to achieve a cryogenic state. Liquid nitrogen was added until the silicone was fully immersed in a bath of the nitrogen. Material was ground. The time required for sufficient grinding will vary depending on the amount of feed stock placed in the grinding unit.
   c. Step 1b was repeated.
   d. Ground material was dumped into a filtering sieve.
2. Filtering the Particulate
   a. The ground silicone was pushed around the sieve screen and the sides of the sieve were tapped to agitate the silicone which loosened the particles and allowed them to fall through the screen in to the collection bin. This was continued until most of the fine particles had been filtered from the feed and a sufficient amount was collected.
3. Dipping and Enhancing the Tissue Expander
   a. Holding the mandrel upside down, it was slowly dipped into uncured silicone dispersed in a solvent. Excess silicone was allowed to drip off the mandrel.

b. The mandrel was then placed in an oven for approximately 12–15 minutes at 54° C. (130° F.). The mandrel was removed.

c. If the dip appeared acceptable, steps 3a and 3b were repeated until proper thickness was obtained.

d. The mandrel was then placed in the oven for 30 minutes at 54° C. (130° F.). The mandrel was removed and checked for defects such as contaminants, bubbles or tears. The mandrel was then placed in an oven for 30 minutes at 130° C. (266° F.).

e. The mandrel was then removed from the oven and carefully placed in distilled water to cool.

f. After mandrel had cooled, step 3a was repeated.

g. The mandrel was placed in the oven for 2–3 minutes at 54° C. (130° F.) in order to set the silicone.

h. The mandrel was then removed from the oven.

i. Filtered particles from step 2a were shaken over the mandrel until the entire surface was fully covered.

j. With an air compressor, held a blow gun approximately 1½ to 2 feet away from the enhanced mandrel. With a series of shots of air, blew off the excess silicone particles being careful not to upset the tacky, underlying silicone layer. Examined the mandrel to insure complete particulate coverage.

k. The mandrel was placed in the oven for 30 minutes at 54° C. (130° F.). The mandrel was then placed in the oven for an additional 30 minutes at 130° C. (266° F.) to fully cure the silicone.

l. Removed from the oven and gently placed the mandrel in distilled water to cool.

m. After about 5 minutes, removed the mandrel from the water and wiped dry with a towel. This not only will dry the mandrel but will also remove some of the remaining excess particles.

4. Applying the Top Coat a. Repeated 3a, using a solvent thinned silicone and immediately placed the mandrel in a vacuum jar and removed the air from the jar. This helped to expel the small bubbles from the mandrel surface.

b. After approximately 15–20 minutes in the vacuum jar, the mandrel is removed and placed it in the oven for 30–45 minutes at 54° C. (130° F.).

c. Fully cured in the oven for 30 minutes at 130° C. (266° F.).

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. An improved implantable device for implantation in humans having an outer membrane comprising:
   a) an enhanced, random sculptured, undulating, irregular, substantially smooth outer membrane surface of smoothly transitioned peaks, valleys, slopes and terraces without substantial indentations or interstices for providing device anchoring in the human body with minimal human-implantable device interface encapsulation, capsular contraction, fibrous capsule generation, trauma and infection, wherein said outer membrane surface is comprised of stacked particles being substantially tetrahedral in shape.

2. The improved implantable device of claim 1, wherein the average differential height from the peaks to the outer membrane surface is in a range of 800 μm to 2500 μm.

3. The improved implantable device of claim 1, wherein the improved implantable device is a tissue expander.

4. The improved implantable device of claim 1, wherein the improved implantable device is a breast implant.

5. The improved implantable device of claim 1, wherein the device is made of silicone rubber.

6. The improved implantable device of claim 1, wherein the tetrahedral shaped particles have an average size of 300 μm to 600 μm.

7. The improved implantable device of claim 1, wherein the spaces between the peaks are about 600 μm.

8. The improved implantable device of claim 7, wherein said stacked particles have an average size of 300 μm to 600 μm.

9. The improved implantable device of claim 1, wherein said particles are comprised of cryogenically ground material.

10. An improved implantable device for implantation in humans having a outer membrane comprising:
    a) an enhanced, random, sculptured, undulating, irregular, substantially smooth outer membrane surface of smoothly transitioned peaks and valleys for providing device anchoring in the human with minimal human-implantable device interface encapsulation, capsular contraction, fibrous capsule generation, trauma and infection, wherein said peaks are comprised of particles being substantially tetrahedral in shape and being spaced about 600 μm.

11. The improved implantable device of claim 10, wherein the improved implantable device is a tissue expander.

12. The improved implantable device of claim 10, wherein the average height differential between the peaks and the outer membrane surface is in a range of 800 μm to 2500 μm.

13. The improved implantable device of claim 10, wherein said stacked particles have an average size of 300 μm to 600 μm.

14. The improved implantable device of claim 10, wherein said outer membrane surface is comprised of an intermediate textured surface and a top coat surface.

15. The improved implantable device of claim 14, wherein said intermediate textured surface is comprised of a first layer bonded to polymeric particles distributed over the surface of said first layer.

16. The improved implantable device of claim 15, wherein said top coat surface is applied over said polymeric particles and is bonded to said intermediate textured surface.

17. The improved implantable device of claim 10, wherein said peaks are comprised of stacked silicone rubber particles being substantially tetrahedral in shape.

18. An improved implantable body for implantation in humans comprising:
    a) a soft, flexible outer membrane forming an enclosure for receiving a filler material; and
    b) an enhanced, undulating, random sculptured, irregular, substantially smooth surface of peaks, valleys, slopes and terraces without interstices and substantial indentations disposed over at least a portion of said outer membrane, said undulating surface formed by:
       i) providing an elastomeric material suitable for use as an implant, having a tacky surface;
       ii) depositing a random distribution of cured polymeric particles which stack on one another on said tacky surface to form an intermediate textured surface, said particles being constructed of silicone and having an average diameter in a range of 300 μm to 600 μm;

iii) curing said intermediate textured surface;
iv) applying a layer of uncured elastomeric material over said intermediate textured surface; and
v) curing said intermediate textured surface having said applied layer of uncured elastomeric material for forming said undulating textured surface.

19. The implantable body of claim 18, further comprising a filler material contained within said outer membrane.

20. The implantable body of claim 18, wherein said elastomeric material having a tacky surface is uncured silicone rubber dispersed in solvent.

21. The implantable body of claim 18, wherein said enhanced surface is comprised of cryogenically ground silicone particles.

22. The implantable body of claim 18, wherein the particles are substantially tetrahedral in shape.

23. The implantable body of claim 18, wherein the spacing between said cured polymeric particles on said tacky surface is about 600 µm.

24. The implantable body of claim 18, wherein the uncured elastomeric material is silicone rubber.

25. The implantable body of claim 18, wherein said step of curing said intermediate textured surface includes heating to a temperature between 130° F. and 270° F. for one hour.

26. The implantable body of claim 25, wherein said step of curing said intermediate textured surface having said applied layer of uncured elastomeric material includes heating to a temperature between 130° F. and 270° F. for one hour.

27. The improved implantable device of claim 18, wherein the mean peak surface height differential is in a range of 800 µm to 2500 µm.

28. The improved implantable device of claim 18, wherein said outer membrane surface is comprised of an intermediate textured surface and a top coat surface.

29. The improved implantable device of claim 28, wherein said intermediate textured surface is comprised of a first layer bonded to polymeric particles distributed over the surface of said first layer.

30. The improved implantable device of claim 29, wherein said top coat surface is applied over said polymeric particles and is bonded to said intermediate textured surface.

31. An improved implantable body for implantation in humans comprising:
a) a soft, flexible outer membrane forming an enclosure for receiving a filler material; and
b) an enhanced, undulating, random sculptured, irregular, substantially smooth surface of peaks, valleys, slopes and terraces without interstices and substantial indentations disposed over at least a portion of said outer membrane, said undulating surface formed by:
i) providing an elastomeric material suitable for use as an implant, having a tacky surface;
ii) depositing a random distribution of cured polymeric particles which stack on one another on said tacky surface to form an intermediate textured surface, said particles being constructed of silicone and being substantially tetrahedral in shape;
iii) curing said intermediate textured surface;
iv) applying a layer of uncured elastomeric material over said intermediate textured surface; and
v) curing said intermediate textured surface having said applied layer of uncured elastomeric material for forming said undulating textured surface.

32. An improved implantable device for implantation in humans having an outer membrane comprising:
a) an enhanced, random sculptured, undulating, irregular, substantially smooth outer membrane surface of smoothly transitioned peaks, valleys, slopes and terraces without substantial indentations or interstices for providing device anchoring in the human body with minimal human-implantable device interface encapsulation, capsular contraction, fibrous capsule generation, trauma and infection, wherein said enhanced surface is comprised of stacked particles having an average diameter in a range of 300 µm to 600 µm and wherein said particles are substantially tetrahedral in shape.

* * * * *